US00PP29419P2

(12) United States Plant Patent
Klemm et al.

(10) Patent No.: US PP29,419 P2
(45) Date of Patent: Jun. 19, 2018

(54) ***CALIBRACHOA* PLANT NAMED 'KLECA16371'**

(50) Latin Name: ***Calibrachoa* sp.**
Varietal Denomination: KLECA16371

(71) Applicant: Klemm+Sohn GmbH & Co. KG, Stuttgart (DE)

(72) Inventors: Nils Klemm, Stuttgart (DE); Anita Stöver, Ostfildern (DE)

(73) Assignee: Klemm+Sohn GmbH & Co. KG, Stuttgart (DE)

( * ) Notice: Subject to any disclaimer, the term of this patent is extended or adjusted under 35 U.S.C. 154(b) by 0 days. days.

(21) Appl. No.: 15/731,832

(22) Filed: Aug. 9, 2017

(30) Foreign Application Priority Data

Mar. 27, 2017 (CA) ..... PBR 17-9147

(51) Int. Cl.
*A01H 5/02* (2018.01)

(52) U.S. Cl.
USPC ..... Plt./413
CPC ..... *A01H 5/02* (2013.01)

(58) Field of Classification Search
USPC ..... Plt./413
CPC ..... A01H 5/02
See application file for complete search history.

*Primary Examiner* — Kent L Bell
(74) *Attorney, Agent, or Firm* — Bethany R. Roahrig; Barbara Campbell; Cochran Freund & Young LLC

(57) ABSTRACT

A new *Calibrachoa* plant particularly distinguished by violet and white star patterned flowers with yellow throats and a semi-upright plant habit, is disclosed.

1 Drawing Sheet

Genus and species: *Calibrachoa* sp.
Variety denomination: 'KLECA16371'.

CROSS REFERENCE TO RELATED APPLICATIONS

The present application claims priority to Canadian Plant Breeder's Rights Application number 17-9147, as filed on Mar. 27, 2017. Plant Breeder's Rights for 'KLECA16371' were also applied for in Europe on Jun. 30, 2017 (Application number 2017-1694). 'KLECA16371' has not been made publicly available or sold more than one year prior to the effective filing date of this application.

BACKGROUND OF THE NEW PLANT

The present invention comprises a new and distinct variety of *Calibrachoa*, botanically known as *Calibrachoa* sp., and hereinafter referred to by the variety name 'KLECA16371'. 'KLECA16371' originated from a controlled cross conducted in Stuttgart, Germany in the summer of 2013, between the proprietary female *Calibrachoa* variety 'CA-2013-0494' (unpatented) and the proprietary male *Calibrachoa* variety 'CA-2013-0187' (unpatented).

The seeds were sown and plants were grown for evaluation. A plant was selected in May 2014 which had violet and white star patterned flowers with yellow throats and was subsequently named 'KLECA16371'. In May 2014, 'KLECA16371' was first vegetatively propagated by tip cuttings in Stuttgart, Germany. 'KLECA16371' was found to reproduce true to type in successive generations of asexual propagation via tip cuttings.

SUMMARY

The following are the most outstanding and distinguishing characteristics of this new variety when grown under normal horticultural practices in Stuttgart, Germany.

1. Violet and white star patterned flowers with yellow throats; and
2. A semi-upright plant habit.

DESCRIPTION OF THE PHOTOGRAPH

This new *Calibrachoa* plant is illustrated by the accompanying photograph which shows the flowers and foliage of the plant. The photograph is of a nine-week-old plant grown in a greenhouse in Stuttgart, Germany in June 2016. The colors shown are as true as can be reasonably obtained by conventional photographic procedures.

DESCRIPTION OF THE NEW VARIETY

The following detailed descriptions set forth the distinctive characteristics of 'KLECA16371'. The data which define these characteristics were collected from asexual reproductions carried out in Stuttgart, Germany. Data was collected on plants grown 20 weeks from sticking outdoors in Stuttgart, Germany in June 2017. Color references are to The R.H.S. Colour Chart of The Royal Horticultural Society of London (R.H.S.), 5$^{th}$ edition (2007).

Classification:
*Family.*—Solanaceae.
*Species.*—*Calibrachoa* sp.
*Common name.*—*Calibrachoa.*

Parentage:
*Female.*—Proprietary *Calibrachoa* 'CA-2013-0494' (unpatented).
*Male.*—Proprietary *Calibrachoa* 'CA-2013-0187' (unpatented).

Plant description:
*Life cycle.*—Annual.
*Form.*—Short-lived subshrubs.
*Habit.*—Semi-upright.

*Height (from soil line to top of foliage)*.—16.0 cm.
*Spread*.—50.0 cm.

Propagation: Vegetatively propagated.
*Type cuttings*.—Tip cuttings.
*Time to produce a rooted cutting*.—3 weeks.

Stems:
*Stem color*.—RHS 145A.
*Pubescence*.—Absent.
*Stem diameter*.—0.2 cm to 0.4 cm.
*Stem length*.—23.0 cm. From soil line to first node: 1.0 cm.
*Internode length*.—2.5 cm.

Leaves:
*Arrangement*.—Opposite.
*Shape*.—Elliptic.
*Apex*.—Obtuse.
*Base*.—Attenuate.
*Margin*.—Ciliate.
*Surface*.—Smooth.
*Surface pubescence*.—Absent.
*Venation*.—Arcuate.
*Venation color*.—Upper surface: RHS 144C. Lower surface: RHS 144D.
*Length*.—2.6 cm.
*Width*.—0.9 cm.
*Color*.—Upper surface: RHS 137B. Lower surface: RHS 137D.
*Fragrance*.—Absent.

Flowers:
*Flowering habit*.—Single flowers.
*Flower type*.—Determinate inflorescence.
*Flowering requirements*.—A minimum of light sun is required.
*Duration of flowers*.—6 days.
*Corolla*.—Smooth texture.
*Shape*.—Funnel form.
*Fragrance*.—Absent.

Flower buds:
*Surface*.—Smooth.
*Length*.—1.8 cm.
*Diameter*.—0.4 cm.
*Shape*.—Irregular to oblong.
*Color*.—RHS N81C with very strong conspicuousness of veins RHS N79A.

Peduncle:
*Length*.—1.5 cm.
*Diameter*.—0.1 cm.
*Color*.—RHS 145A.
*Texture*.—Smooth.
*Anthocyanin color*.—RHS N79A.

Flower description:
*Flower depth*.—2.3 cm.
*Flower tube length*.—2.0 cm.
*Flower tube diameter*.—0.7 cm.
*Flower diameter*.—3.4 cm.
*Pedicel color*.—RHS 145A.
*Calyx*.—Funnel-shaped.

Sepals:
*Shape*.—Lanceolate.
*Apex*.—Acute.
*Margin*.—Entire.
*Length*.—1.0 cm.
*Diameter*.—0.3 cm.
*Sepal color*.—Upper surface: RHS 143A. Lower surface: RHS 143B.

Petals:
*Shape*.—Obcordate.
*Length*.—1.7 cm.
*Apex*.—Truncate.
*Margin*.—Entire.
*Base*.—Open and fused in the tube.
*Pubescence*.—Absent.
*Lobe length*.—1.7 cm.
*Lobe width*.—1.6 cm.
*Color*.—Lobe color: Upper surface: Main color is RHS N81A (juvenile) and RHS N81D (mature); medium area at transition to corolla tube is RHS 83A; medium area along the fused parts of the corolla lobes is RHS NN155C. Lower surface: Main color is RHS N81C (juvenile) and RHS N81D (mature); medium area along the fused parts of the corolla lobes is RHS NN155B. Corolla tube color: Inner: RHS 9B with medium conspicuousness of veins RHS N79A. Outer: RHS 9D with very strong conspicuousness of veins RHS N79C.
*Fragrance*.—Absent.

Reproductive organs:
*Stamen number*.—5. Anther color: RHS 7A. Filament color: RHS 145C. Pollen color: RHS 7A.
*Ovary*.—Placenta arrangement: Ovate. Pistil number: 1. Pistil length: 1.2 cm. Stigma color: RHS 143B. Style length: 0.9 cm. Style color: RHS 150C.
*Fruit/seed set*.—Seed is sometimes observed but additional information is not available.
*Disease/insect resistance*.—None observed.

COMPARISON WITH PARENTAL LINES AND KNOWN VARIETY

'KLECA16371' is distinguished from its parents as described in Table 1:

TABLE 1

Comparison with Parental Lines

| Trait | Variety 'KLECA16371' | Female parent 'CA-2013-0494' | Male parent 'CA-2013-0187' |
|---|---|---|---|
| Main flower (Upper Surface) | Juvenile RHS N81A Mature RHS N81D | RHS 67B | RHS 4B |

'KLECA16371' is most similar to the *Calibrachoa* plant named SUPERBELLS 'Evening Star', also known as 'USCAL42202' (U.S. Plant Pat. No. 27,008). Differences between the two varieties are described in Table 2:

TABLE 2

Comparison with Similar Variety

| Trait | Variety 'KLECA16371' | Commercial line 'USCAL42202' |
|---|---|---|
| Distribution of secondary color of flower | Medium along the fused parts of the corolla lobes (RHS NN155C) | No star pattern, only very large marking at transition to corolla tube |

We claim:

1. A new and distinct variety of *Calibrachoa* plant named 'KLECA16371' as illustrated and described herein.

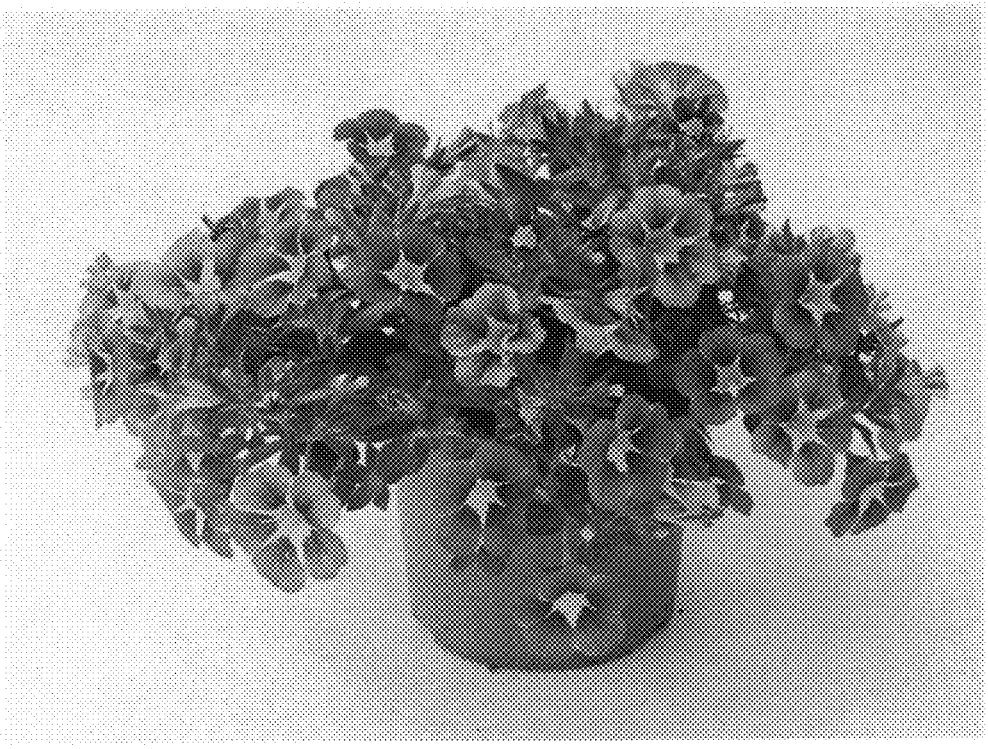

* * * * *